(12) United States Patent
Mathur et al.

(10) Patent No.: US 6,326,202 B1
(45) Date of Patent: Dec. 4, 2001

(54) **STABLE HIGH GINSENOSIDE-YIELDING CALLUS LINE OF *PANAX QUINQUEFOLIUM* (AMERICAN GINSENG) AND A METHOD FOR DEVELOPING SUCH STABLE HIGH GINSENOSIDE-YIELDING CALLUS LINE**

(75) Inventors: Archana Mathur; Ajay Kumar Mathur; Girish Chandra Uniyal; Mahesh Pal; Rajender Singh Sangwan, all of Lucknow (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 09/420,349

(22) Filed: Oct. 19, 1999

(51) Int. Cl.⁷ .................................................... C12N 5/02
(52) U.S. Cl. .......................................... 435/410; 435/420
(58) Field of Search ...................... 435/410, 420

(56) References Cited
PUBLICATIONS

Tsutomu Furuya, "Saponins (Ginseng Saponins)", Chapter 12 of *Cell Culture and Somatic Cell Genetics of Plants*, vol. 5, 1988, Academic Press, Inc., pp. 213–234.

Shinji Inomata et al., "Growth pattern and ginsenoside production of Agrobacterium–transformed *Panax ginseng* roots", *Plant Cell Reports*, 1993, pp. 681–686.

Lakafumi Yoshikawa et al., Saponin production by cultures of *Panax ginseng* transformed with *Agrobacterium rhizogenes*, *Plant Cell Reports*, 1987, pp. 449–453.

T. Furuya et al., "Regulation of Saponin Production in Callus Cultures of *Panax ginseng* [1]", School of Pharmaceutical Sciences, Kitasato University, Japan, 1982, pp. 200–204.

K.T. Choi, "*Panax ginseng* C.A. Meyer: Micropropagation and the In Vitro Production of Saponins", *Biotechnology in Agriculture and Forestry*, vol. 4, Medicinal and Aromatic Plants 1, 1988, pp. 485–500.

*Primary Examiner*—Leon B. Lankford, Jr.

(57) ABSTRACT

The invention provides stable high ginsenoside-yielding callus lines of *Panax quinquefolium* (American Ginseng). The callus lines are useful in the industrial production of ginsenosides for use in a variety of ginseng preparations.

18 Claims, 2 Drawing Sheets

(1 of 2 Drawing Sheet(s) Filed in Color)

SEQUENCE LISTING

<160> NUMBER OF SEQ ID NOS: 6

<210> SEQ ID NO 1
<211> LENGTH: 10
<212> TYPE: DNA
<213> ORGANISM: Artificial sequence
<220> FEATURE:
<223> OTHER INFORMATION: primer

<400> SEQUENCE: 1 cgcagtactc

```
<210> SEQ ID NO 2
<211> LENGTH: 10
<212> TYPE: DNA
<213> ORGANISM: Artificial sequence
<220> FEATURE:
<223> OTHER INFORMATION: primer

<400> SEQUENCE: 2
gtcctactcg                                                              10

<210> SEQ ID NO 3
<211> LENGTH: 10
<212> TYPE: DNA
<213> ORGANISM: Artificial sequence
<220> FEATURE:
<223> OTHER INFORMATION: primer

<400> SEQUENCE: 3
ctacacaggc                                                              10

<210> SEQ ID NO 4
<211> LENGTH: 10
<212> TYPE: DNA
<213> ORGANISM: Artificial sequence
<220> FEATURE:
<223> OTHER INFORMATION: primer

<400> SEQUENCE: 4
gtccttagcg                                                              10

<210> SEQ ID NO 5
<211> LENGTH: 10
<212> TYPE: DNA
<213> ORGANISM: Artificial sequence
<220> FEATURE:
<223> OTHER INFORMATION: primer

<400> SEQUENCE: 5
gtcctcaacg                                                              10

<210> SEQ ID NO 6
<211> LENGTH: 10
<212> TYPE: DNA
<213> ORGANISM: Artificial sequence
<220> FEATURE:
<223> OTHER INFORMATION: primer

<400> SEQUENCE: 6
ctactaccgc                                                              10
```

STABLE HIGH GINSENOSIDE-YIELDING CALLUS LINE OF *PANAX QUINQUEFOLIUM* (AMERICAN GINSENG) AND A METHOD FOR DEVELOPING SUCH STABLE HIGH GINSENOSIDE-YIELDING CALLUS LINE

FIELD OF THE INVENTION

The present invention relates to a stable high ginsenoside-yielding callus line of *Panax quinquefolium* (American ginseng) developed from root explants and a process for the development of these callus lines. More particularly, the invented callus line has a distinct morphological marker of purple pigmentation and saponin yield comparable in quantity and quality to that of normal roots.

The invention provides a viable alternate option to boosting the industrial production of ginseng saponins (ginsenosides) which are in high demand in market as important ingredients of health tonics and anti-aging drug preparations.

BACKGROUND

Ginsenosides (triterpene glycosides) extracted from roots of 4–7 years old plants of ginseng (common name for Panax species) are important constituents of herbal health care products today. Owing to their strong immuno-modulatory, adaptogenic and aphrodisiac actions, ginseng saponins are widely prescribed in several conditions of health disorders such as anaemia, diabetes, asthma, neuroaesthemia, dyspepsia, convulsion and even in cancer and AIDS. Priced at 750–1000 US $ per kg and with an annual global production of 35–40 thousand tons, Panax roots are the fourth largest selling herbal healthcare product today. Korea, China and Japan have the major share in the global supply of ginseng roots. [Indian pharmaceutical companies import about 400–500 tons of Panax root powder annually.] The chief source of ginseng roots are *P. ginseng* (Korean panax), *P. quinquefolium* (American panax) and *P. notoginseng* (Chinese panax). The Indian congeners i.e. *P. pseudoginseng* and *P. sikkimensis* Ban., growing wild in the sub-Himalayan zones (Darjeeling, Sikkim, Arunachal Pradesh etc.) though found to be on par in saponin quality and content with their oriental counterparts, have not yet been commercially exploited. Traditional field cultivation of Panax sp. is very slow and labour intensive. It takes 18–22 months for the seed to germinate (following 2–3 stratification cycles to break seed dormancy) and an extended gestation period of 3–5 years for the crop to mature and provide economic root biomass yield and quality of saponins. Tissue culture based strategies for rapid propagation (micro-cloning) and in vitro ginsenoside production in Panax, therefore, hold immense promise and potential.

PRIOR ART REFERENCES

These are many reports on tissue culture studies particularly, in vitro ginsenoside production in cell suspension cultures, of Korean ginseng—*P.ginseng* [Boitechnology in Agriculture & Forestry Vol. 4(1) (Ed) Y. P. S. Bajaj pp 484–500 (1988); Cell Culture and Somatic Cell Genetics of Plants Vol. 5 (Ed) I. K. Visil (1988)pp. 213–234, J. Biotechnol 52:121–126 Process Biochem, 33:69–74 (1998)]. The maximum ginsenoside level detected in cell culture of ginseng has been reported to be 16 mg/g. dry wt. (Agri Cell Rep., February, 1994). Possibility of ginsenoside production in genetically transformed hairy roots has also been indicated in *P.ginseng* [Pl. Cell Rep. 12: 681–686; (1993), Ibid 15: 555–560) (1996), Phytochemistry 49:1929–1934 (1998)]. In contrast there have been very few reports concerning *P. quinquefolium* cell and tissue cultures [Phytochemistry 35: 1221–1225, (1994), Process Biochem., 33:69–74 (1998)]. The applicants, during their research, had earlier shown that callus and cell suspension cultures of *P. quinquefolium* are also capable of producing characteristic ginsenosides in vitro [Phytochemistry 35:1221–1225 (1994)]. The crude ginsenoside content (i.e. 0.56% and 0.65% for callus and cell cultures, respectively) and ratio of Rb and Rg group of ginsenosides of these wild line cultures were found to vary with their age (days after subculture) during a 5 week culture cycle. The possibility of isolating high ginsenoside yielding lines of *P. quinquefolium*, specifically rich in different ginsenoside fractions, was first hypothesized by the applicants in this report. The present invention is an outcome of the continued efforts made by the applicants in this direction and accordingly, the applicants have now developed a high-yielding callus line with a crude ginsenoside level as high as 1.21% f.wt. that matches well with that in 3–4 years old roots of field grown plants [Shoyakugaku Zosshi 32:96 (1978), J. Herb Spices & Med. Pl. 3:41–50 (1995)]. Recent market trends show that because of extremely high price of wild roots of *P. ginseng*, the demand for *P. quinquefolium* has increased dramatically and is 5–10 times more expensive than its oriental counterparts [Pl. Med. 61:466–469 (1996)].

Figure 1:
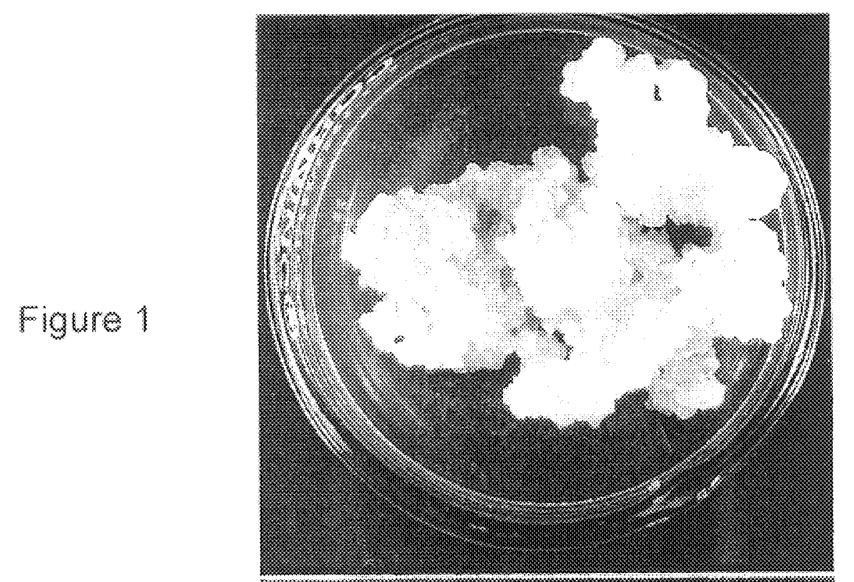
FIG. 1 is a photograph that represents a mild callus line of *Panax quinquefolium*.

The novelties of the inventions are as follows:

(a) The invention for the first time, provides a stable high-ginsenoside yielding callus line of *P. quinquefolium* whose saponin content is comparable in yield and quality to that of field grown plants, (b) The procedure outlines the formulation of a callus culture maintenance medium [modified MS medium with double the amount of organic adjuvants+200 mg/l myoinositol+2, 4-D (1.0 mg/l)+Kinetin (0.25 mg/l)] for callus maintenance and multiplication and incubation environment such as continuous light (3000 Lux) and temperature 28±2° C. that support sustained growth and stable ginsenoside yield for over four and half years, (c) The invention has resulted in identifying the parameters, such as inoculum age, inoculum to medium ratio, tissue harvesting schedule, media pH, and extraction, TLC densitometry and HPLC analysis of the crude ginsenoside, that are required for further scaling up of the isolated line, (d) The isolated callus line has a morphologically distinguishable feature, characteristic DNA profile and a stable chemical fingerprint. FIG. 1 depicts the characteristic purple pigmentation in the callus cells of the isolated line in comparison to pale white non-pigmented wild line counterpart. The morphological appearance is as nearly true as is reasonably possible to make the same in coloured illustration of this marker character, (e) The isolated callus line has been shown to grow and accumulate ginsenoside in amounts and quality on medium having cheap market grade sugar as energy source in comparison to the conventionally employed costly analytical grade sucrose. This is a vital step towards cost reduction strategies for commercial utilisation of such tissue culture lines, (f) The isolated callus line has all the desired attributes that enable it to be exploited on a commercial basis.

Objects

The main object of the present invention is to provide a stable high ginsenoside-yielding callus line of *Panax quinquefolium* (American ginseng), developed from root explants and a process for the development of said callus lines, obviating the drawbacks of the earlier methods.

Another object of the present invention is to isolate a callus line with saponin yield comparable in quantity and quality to that of normal roots so as to devise an in vitro process for the production of these health care compounds on a commercially feasible scale.

Still another object of the present invention is to identify in vitro growth conditions and other experimental parameters for commercialisation and in vitro production of *Panax quinquefolium*.

Yet another object of the present invention is to reduce the cost of ginsenoside production in vitro by use of cheaper carbohydrate sources.

One more object of the present invention is to identify morphological marker(s), genetic marker (DNA fingerprint) and chemical fingerprint of the isolated high-yielding line.

BRIEF DESCRIPTION OF THE ACCOMPANYING DRAWINGS

The file of this patent contains at least one photograph executed in color. Copies of this patent with color photographs will be provided by the Patent and Trademark Office upon request and payment of the necessary fee.

DETAILED DESCRIPTION

Figure 3:
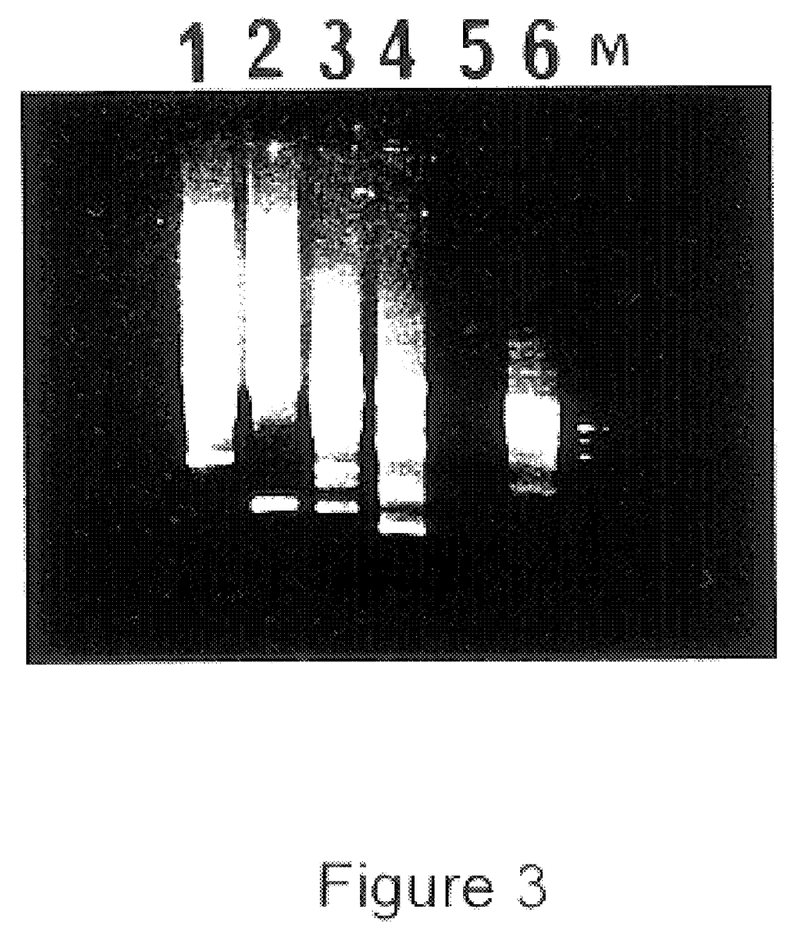
FIG. 3 is a photograph that represents the DNA profile of the selected callus line of *Panax quinquefolium*.

Accordingly, the present invention provides a stable high ginsenoside—yielding callus line of *Panax quinquefolium* (American ginseng) from root explant having:

(a) purple pigmentation, (b) growth Index of 204.8 to 246.01 in about 45 days of culture, (c) ginsenoside yield of 0.94 to 1.33% f.wt. in about 45 days of culture, (d) yield of Rb group of ginsenosides 49 to 55% from the crude extract in about 45 days of culture, (e) yield of Rg group of ginsenoside of 35–49% from crude extract in about 45 days of culture, and (f) characteristic DNA profile wherein the lanes 1, 2, 3, 4, 5, and 6 as represented in FIG. 3, wherein the PCR amplified fragments produced by the template megabase genomic DNA with the primers 5' CGCAGTACTC 3' (SEQ ID NO: 1), 5' GTCCTACTCG 3' (SEQ ID NO: 2), 5° CTACACAGGC 3' (SEQ ID NO: 3), 5' GTCCTTAGCG 3' (SEQ ID NO: 4), 5' GTCCTCAACG 3' (SEQ ID NO: 5), 5' CTACTACCGC 3' (SEQ ID NO: 6), respectively, are shown and Lane Mw shows the standard size markers of a ladder at 100 bp intervals from 1000 bp downwards.

In an embodiment, the invention provides a method for the development of a stable high ginsenoside-yielding callus line from root explants, comprising the steps of:

(a) establishing of the aseptic callus cultures from root explants on basal medium modified after Murashige and Skoog medium to obtain primary callus, (b) transferring the primary calli to medium II for optimal growth, (c) multiplying and maintaining the callus for more than 2 years by regular sub-culturing in medium II every six to seven weeks under temperature 28±2° C., 1000–2000 lux light intensity and 70 to 80% relative humidity;

(d) obtaining the fragile and pale white calli, (e) isolating the high yielding purple pigmented callus occurring as spontaneous variant from $20^{th}$ sub-culture, (f) enriching the isolated purple pigmented variant through selection and cell aggregate cloning in at least seven subsequent sub-cultures, and (g) proliferating the enriched callus line by using culture Medium III and incubating the callus culture in continuous light of 3000–4000 lux intensity to obtain high yielding callus line.

In an embodiment of the invention the root explants are obtained from at least 3 years old *Panax quinquefolium* plants.

In yet another embodiment, the roots are cut into 2–7 mm long small explant pieces which are washed thoroughly in water at least 4 times to remove dirt and contaminants.

In a further embodiment, the root explants are sterilized by treatment with centrimide for a period of about 5–10 minutes and with mercuric chloride for about 10–30 seconds.

In another embodiment of the invention, the medium used in step (a) is the basal medium modified after Murashige and Skoog's (1962) medium supplemented with 2–4 mg/l glycine, 200 mg/l myoinositol, 10 mg/l thiamine hydrochloride, 10 mg/l pyridoxine hydrochloride and 5 mg/l nicotinic acid.

In a further embodiment, Medium II used in step (b) is obtained by addition of 2,4-dichlorophenoxyacetic acid (0.5–2.0 mg/l) and kinetin (0.25–0.50 mg/l) to the basal medium for optimal callus induction.

In an another embodiment, Medium III used in step (g) comprises nutrient salts of basal medium, 200 mg/l myoinositol, 2.0–4.0 glycine, 0.5–1.0 mg/l nicotinic acid, 0.5–2.0 mg/l pyridoxine HCl and 0.2–0.4 mg/l thiamine HCl, 2,4-D (0.1–0.5 mg/l) and Kinetin (0.25–0.50 mg/l) for optimal growth of the selected line.

In yet another embodiment of the present invention, chemical extraction of the ginsenosides from freshly harvested callus (5 to 45 days or 1 to 5 months old) was done with methanol (100%, 4 times), redissolving the dried extract in water soluble portion and finally extracting this water portion with n-Butanol saturated with water (4 times), collecting the n-Butanol fraction, centrifuging it and collecting the supernatant, drying it under vacuum.

In yet another embodiment of the present invention, the selected callus line is genetically characterised through molecular marker patterns generated using the cell line genomic DNA as template in the randomly primed polymerase chain reaction (RP-PCR) assays.

In yet another embodiment of the present invention the content and quality of various ginsenoside fractions may be monitored and identified by TLC densitometry and HPLC.

In still another embodiment of the present invention carbohydrate sources used may be selected from sucrose, market grade sugar, molasses treated with EDTA and charcoal.

The callus line of the invention has faster growth rate (Growth index=204.80–246.01) giving rise to increased (about 7.5 folds) biomass production than in non-selected wild line (Growth index=21.40–36.56) in about 45 days of culture.

It also has increased crude ginsenoside yield. It is about 4 times more in selected callus line (0.94–1.33%f.wt) in comparison to that of wild line (0.24–0.37%) in about 45 days of culture. The applicants observed increased yields of Rb and Rg group of ginsenosides. After about 45 days of culture the crude extract has 49–55% of ginsenosides of the Rb group and 35–49% of ginsenosides of the Rg group in the selected line as compared to 6–8% Rb group and 33–45% Rg group of ginsenosides in the wild line.

Brief methodology of the present process includes:

(a) Establishment of aseptic callus cultures of the wild line and selection of the high ginsenoside—yielding line.

Figure 2:
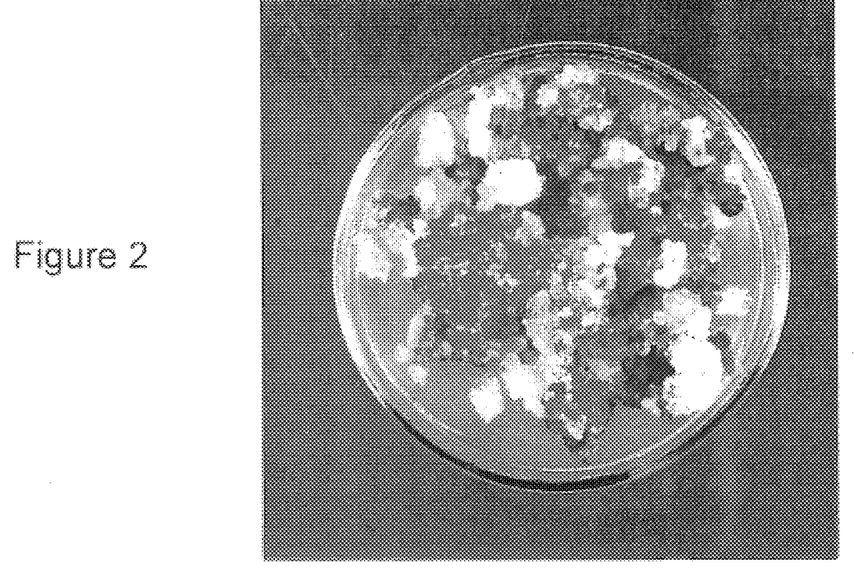
FIG. 2 is a photograph that depicts the characteristic purple pigmentation in the callus line of the invention

The wild line utilised in this study was generated as reported by the applicants earlier (Phytochemistry 35: 1221–1225, 1994). Briefly, the roots of a 3 years old *P. quinquefolium* plant grown at CIMAP (Central Institute of Medicinal and Aromatic Plants, Lucknow, India) experimental Farm at Bonnera (Jammu and Kashmir; 3500 altitude) were cut into small explant pieces (2–7 mm long). The explants were washed in water 4–5 times to ensure that all dirt was removed. The explant surface was sterilized with centrimide (10 min) and 0.1% $HgCl_2$ (10 seconds) and horizontally implanted onto the agar-gelled medium. The basal medium (BM) used during the course of the present invention was of Murashige and Skoog (1962; Physiol. Plant, 15:473–497); and consisted of (in mg/l) $NH_4NO_3$ (1650), $KNO_3$ (1900), $KH_2PO_4$ (170), $MgSO_4.7H_2O$ (370), $CaCl_2.2H_2O$ (440), $ZnSO_4.7H_2O$ (8.60), $H_3BO_3$ (6.20), $MnSO_4.4H_2O$ (22.30), KI (0.83), $CuSO_4.5H_2O$ (0.025), $CoCl_2.6H_2O$ (0.025), $Na_2MoO_4.2H_2O$ (0.25), $Na_2EDTA$ (37.25), $FeSO_4.7H_2O$ (27.85), glycine (2.0), nicotinic acid (0.50), pyridoxine HCI (0.50), thiamine HCI (0.10), myo-inositol (100), sucrose (30,000) and agar (7,000). Keeping in view the high demands for nutrients and organic manure by Panax species during field cultivation, the basal medium (BM) used in this study was modified after Murashige and Skoog (Physiol. Plant. 15: 473–497) by incorporating into MS medium 200 mg/l of myo-inositol, 10 mg/l each of thiamine hydrochloride and pyridoxine HCI and 5 mg/l of nicotinic acid (Medium I). Optimal callus induction occurred when basal medium (BM) was further fortified with 2,4-dichlorophenoxyacetic acid (0.5–1.5 mg/l) and kinetin (0.25–0.50 mg/l) (Medium II). The induced calli were multiplied by regular sub-culturing onto the fresh medium every 6–7 weeks under 2000 Lux light intensity, 28±2° C. temperature and 70–80% relative humidity. The high-yielding callus line was isolated from the wild line (pale-white in appearance) as a spontaneously occurring variant in the form of purple pigmented sector in the 20$^{th}$ subculture cycle. The variant sector was excised and subjected to repeated selection for seven subsequent subculture cycles. The selected line proliferated better when Medium II was replaced with a different callus maintenance medium comprising of nutrient salts of BM,200 mg/l myoinositol, 2.0–4.0 mg/l glycine, 0.5–1.0 mg/l nicotinic acid, 0.5–2.0 mg/l pyridoxine HCI, 0.2–0.4 mg/l thiamine HCl, 0.1–0.5 mg/l 2,4-D and 0.25–0.50 mg/l Kinetin (Medium III). Through this "cell-enrichment" selection technique the pigmented line (FIG. 2) was isolated with stable morphology, characteristic DNA profile (FIG. 3) and fast growth in vitro, and was further subjected to chemical analysis. The selected line requires continuous light of high intensity (3000–4000 lux) for its optimum proliferation and growth in culture.

(b) Growth kinetic studies of the wild and the selected lines.

For the in vitro growth and other culture conditions for improved ginsenoside yield and quality, the calli of the isolated line was subcultured under different nutrient/incubation regimes (treatments) and their Growth index (GI) was calculated as a function of time by following formula.

$$G.I = \frac{F.Wt.\ at\ the\ time\ of\ harvest - Initial\ inoculum}{Initial\ inoculum} \times 100$$

A minimum of 24 replicated cultures/treatment were used for data analysis and the data is expressed as mean performance±SD of all the replicates. All experiments were repeated at least 3 times.

(a) Molecular characterisation of the selected line.

The selected line was genetically characterised through molecular marker patterns generated using the cell line genomic DNA as template in the randomly primed polymerase chain reaction (RP-PCR) assays. The amplification reaction mixture in a final volume of 25 $\mu$l, contained 400 $\mu$M each of dNTP, 1.0 mM $MgCl_2$, 10.0 pmoles of primer, 0.25 units of Taq polymerase and 2.5 $\mu$l Taq buffer (Bangalore Genei, India), 50.0 ng template DNA. After a single pre-PCR cycle of 94° C. (5 min), 35° C. (1.5 min) and 10° C. (15 min), the reaction mixture contents were cycled to 40 times with each cycle consisting of a sequence of 94° C. (1.5 min), 35° (1.5 min) and 72° C. (1.0 min) and were finally given an extension completion incubation of 72° C. for 5 min in a PCR machine (Perkin Elmer Model 2400). At the end of the PCR run, amplification products were separated electrophoretically on a 1.4% agarose in 1×TAE buffer. A mixture of 1000 to 100 base pairs (bp) of ladder of 10 double stranded (ds) DNA fragments were co-electrophoresed to gauge the size (bp) of the amplification products.

(d) Extraction of the crude ginsenoside

Extraction of crude ginsenoside from callus samples was done according to the procedure reported earlier by us [Phytochemistry 35: 1221–1225 (1994)]. The method which was essentially modified after Furuya et al. [Chem. Pharm. Bull. 21:98 (1973)] is briefly explained in the following flow chart:

-continued

Residue redissolved in H₂O and extracted with Hexane (×2)

↓

Hexane layer (discarded) | H₂O soluble part extracted with ether

↓ | ↓

Ether layer (discarded) | H₂O soluble part extracted with n-BuOH saturated with water (×4)

↓

H₂O layer (discarded) | n-BuOH fraction contains crude ginsenosides

↓

Dried under vacuum

↓

Weighed & subjected to TLC and HPLC analyses (e) TLC analysis of crude ginsenoside extract.

The crude ginsenosides were redissolved in HPLC grade methanol, centrifuged at 8000 rpm for 15 minutes and supernatant collected. The crude sample was first spotted on 60 F 254 E-merck pre-coated TLC plates and chromatographed, alongwith known amount of authentic ginsenoside samples using a solvent phase consisting of $CHCl_3:MeOH:H_2O$ (13:7:2). The ginsenoside fractions were visualized by spraying the plates with 10% (v/v) $H_2SO_4$ followed by heating at 100° C. for 10 minutes. Scanning for quantification of these spots was carried out on a dual wavelength densitometer (Shimadzu) at 530 and 700 nm.

(f) HPLC analysis of crude ginsenoside extract.

HPLC of the crude ginsenoside mixture was carried out according to a modified procedure of Solidati and Sticher (Pl. Med. 1980 38:348–357). The analysis was performed on a $C_{18}$ waters $\mu$ Bondapack column (150×3.9 mm) using $CH_3CN:H_2O$:9:16 (flow rate=0.5 ml/minute) as mobile phase for ginsenosides $Rb_1$, $Rb_2$, Rc, Rd, Rf and Ro. The Rt values for these were found to be 7.98, 8.81, 10.63, 13.45, 18.98 and 20.82, respectively. For ginsenoside Re and Rg1 separation, mobile phase used was $CH_3CN:H_2O$:11:39 (the respective Rt values for these were 21.88 and 23.19, respectively). Detection was done at $\lambda$ max=203 nm. While all other authentic ginsenoside fractions were procured from Carl Roth (Germany), ginsenoside Ro was generously gifted by Prof. O. Tankaka (Japan).

The following examples further illustrate the comparison of biomass yield and ginsenoside productivity and effect of inoculum density, harvesting schedule and efficacy of different carbohydrate source on these in wild and selected callus lines of the present invention and should not be construed to limit the scope of the invention:

EXAMPLE 1

Growth kinetics and ginsenoside productivity and quality of the subject callus lines:

Growth characteristics of the selected line was studied and compared with that of the wild line (control) over a culture span of 45 days. Specific growth rates, crude ginsenoside contents and quality were monitored at 10 days interval and the results are depicted in Table 1. The higher biomass and ginsenoside productivity of the selected line became evident from the $25^{th}$ day of incubation and continued up to $45^{th}$ day of culture. The wild line accumulated highest biomass and crude ginsenosides around the $25^{th}$ and the $35^{th}$ day of culture, whereas corresponding values in case of the selected line were acquired on around 40–50 days of culture. The biomass production in terms of growth index is about 7.5 times more in selected line (232.7) in comparison to the wild line (30.2) after 45 days of culture (Table 1). The crude ginsenoside content on fresh weight basis is about 4 times in the selected line (1.21%) in comparison to that of wild line (0.29%). For ginsenoside quality in terms of Rb: Rg fractions, wild line cultures at around 25–30 days were the best, the selected line-again exhibited best profile around 40 days of culture when as high as 53% and 43% of Rb and Rg groups of ginsenosides were produced.

The selected callus line has depicted high stability in terms of its in vitro growth (GI=210.8–292.09), crude ginsenoside content (1.09–1.27% f.wt.) and ginsenoside quality (Rb: Rg ratio=1.12–1.30) for over 20 subculture generations during more than three years tested (Table 2). The Panax cultures in general, showed slightly better growth in winter months (November–February) than in summer months (April–August).

EXAMPLE 2

Effect of inoculum density and harvesting schedule on ginsenoside production and quality:

Harvesting schedule and the amount of initial inoculum for increase productivity of the selected line were studied taking four initial inoculum densities (10–40% w/v), the best growth and saponin yields were obtained when 2–3 months old calli were used at 25–30% initial density (i.e., 10–15 g innoculum/40 ml of the medium). Besides, a 30–35 day culture cycle should be followed if both Rb (particularly $Rb_2$) and Rg (mainly Rg, and Re) groups of ginsenosides are to be extracted (Table 3). The culture span can be reduced to 5–10 days if interest lies more in $Rb_1$ and $Rb_2$ fractions which became very low beyond 40–45 days of incubation. For Rg group of saponins the cultures should be harvested after 3–4 months when Rg1+Re are the major fractions of the ginsenoside pool.

EXAMPLE 3

Comparison of different carbohydrate sources on growth and ginsenoside content in the subject line:

Different carbohydrate energy sources in the medium were tried to observe the efficacy of cheaper substitute for costly sucrose (Table 4). In order to cost economise the in vitro procedure developed in this study, the conventionally used carbon source-sucrose (Rs 250 per kg), which is the most costly ingredient of the nutrient medium, was tried to be substituted with alternate cheaper sources like market grade sugar (Rs. 14–16/kg) and molasses (Rs 1.0 per liter) which is a waste byproduct of sugar industries. While efficacy of market grade sugar was evaluated at 1–4% (w/v) concentration in the callus maintenance medium, molasses was subjected to certain pretreatment (prior to use) to remove inhibitory compounds. For this, 25% (wlv) molasses solution was soaked with activated charcoal (2 g/l) for 2 hours, boiled for 30 minutes and left overnight. It was then filtered (Whatman No.1) and centrifuged. The supernatant was diluted with water (x 50 times) and used 0.3% (v/v) in experiments. Alternately 5% of the molasses (w/v) solution was titrated with 10% (w/v) $Na_2$-EDTA to precipitate EDTA-chalets, kept in the refrigerator overnight, centrifuged and diluted 50 times as above, before using 0.3% (v/v) in the medium. The wild and selected callus lines were grown on medium supplemented with 3% (w/v) sucrose (control), market grade sugar (3% w/v) and charcoal or EDTA treated molasses. The results obtained for biomass yield and crude ginsenoside content after 10 days interval upto 50 days of incubation indicated that while molasses could not sustain callus growth, market grade sugar which is about 15 times cheaper than Analar grade sucrose can be used as a sole energy source for both wild and the selected lines. In fact market grade sugar-containing medium supported 10–15% more biomass gain than sucrose in case of the selected line (Table 4). The crude ginsenoside content in the sugar containing medium also remained as high as in sucrose supplemented medium. HPLC analysis of the saponins also did not indicate any inhibitory effect of sugar on levels of various ginsenoside fractions.

EXAMPLE 4

Effect of supplementation of sodium acetate in the medium on ginsenoside yield:

One of the probable precursors sodium acetate was incorporated in the medium at concentration ranging from 5–50 mg/l. Sodium acetate has been used by other workers (P1. Med. 47:200–204) as a putative precursor for saponin biogenesis. The selected as well as non-selected lines of *P. quinquefolium* (our study) however showed a sharp fall in ginsenoside content (0.06–0.18% f.wt.) at various levels of sodium acetate. Which probably is not an appropriate precursor to be used in such feeding experiments with *P. quinquefolium* calli.

The above mentioned examples clearly indicate that present invention provides a high ginsenoside-yielding purple pigmented callus line of *P. quinquefolium* that can synthesize and accumulate ginsenosides (both in content and quality) that are produced in field grown roots of this plant species. To the best of our knowledge this is the first line of its kind and has all the attributes necessary for the commercial scaling and utilization.

The following tables, i.e., Tables 1 to 4, provide comparisons of biomass yield and production of different ginsenosides, stability of the selected line, effect of culture duration at the time of harvest on quantitative and qualitative spectrum of ginsenosides in the wild and selected callus lines of *P. quinquefolium*, and comparison of the efficacy of different carbohydrate energy sources (supplemented in callus maintenance medium) on biomass yield and crude ginsenoside content of wild and selected callus lines of *P. quinquefolium*, respectively.

TABLE 1

Comparison of change in biomass yield and production of different ginsenosides as a function of culture age in wild and selected callus lines of *P. quinquefolium**

| Days after Inoculation | Callus Line | Growth Index | Crude ginsenoside Content (% f. wt) | Rh group | Rg group | Ro group | Rb:Rg Group |
|---|---|---|---|---|---|---|---|
| 5 | W | 23.5** | 0.10 | 35.43 | 38.00 | 2.40 | 0.93 |
|  | S | 22.3 | 0.32 | 41.23 | 29.98 | 1.89 | 1.37 |
| 15 | W | 11.9 | 0.39 | 3.91 | 22.84 | 1.37 | 0.04 |
|  | S | 24.1 | 0.46 | 17.03 | 7.83 | 1.26 | 0.61 |
| 25 | W | 32.2 | 0.56 | 56.64 | 51.18 | 4.50 | 1.11 |
|  | S | 175.9 | 0.80 | 38.20 | 38.29 | 3.21 | 0.99 |
| 35 | W | 40.8 | 0.26 | 2.94 | 45.41 | 8.60 | 0.07 |
|  | S | 216.2 | 0.97 | 44.92 | 39.42 | 3.82 | 1.14 |
| 45 | W | 30.2 | 0.29 | 7.15 | 40.87 | tr | 0.18 |
|  | S | 232.7 | 1.21 | 53.82 | 43.47 | 4.60 | 1.24 |

*Inoculum size = 25% (10 g/40 ml medium)
**Each value represents the mean of three analysis done at 6, 12 and 18 months of total culture age (4 replicates/analysis)
W Wild line
S Selected line
tr Trace amounts.

TABLE 2

Stability of the selected line in terms of growth index, crude ginsenoside content and ratio of Rb and Rg ginsenoside over a period of three years.

| Total culture age (months) / time of harvest | Growth Index* | Crude ginsenoside Content (% f. wt.) | Ginsenoside quality (% of crude Ginsenoside) | | |
|---|---|---|---|---|---|
| | | | Rb Group | Rg group | Rb Group: |
| 8 (December, 95) | 280.20** | 1.18 | 58.82 | 43.47 | 1.24 |
| 14 (June, 96) | 210.80*** | 1.23 | 31.13 | 45.65 | 1.12 |
| 20 (December, 96) | 290.60 | 1.14 | 50.04 | 39.09 | 1.28 |
| 26 (June, 97) | 239.68 | 1.22 | 49.21 | 37.85 | 1.30 |
| 32 (December, 97) | 292.09 | 1.09 | 9.08 | 40.90 | 1.20 |
| 38 (June, 98) | 248.58 | 1.27 | 52.23 | 40.48 | 1.29 |

*Panax callus cultures show slightly faster growth in winter months than in summer
**Data were collected after 45–50 days of growth in the respective passage.
***All data represent mean of 4 pooled replicates of 6 cultures each

TABLE 3

Effect of culture duration at the time of harvest on quantitative and qualitative spectrum of ginsenosides in the wild and selected callus lines of *P. quinquefolium**

| Culture Duration (months) | Callus Line | Crude ginsenoside (% f. wt.) | Rb1 | Rb2 | Rc | Rd | Rf | Rg1 + Re |
|---|---|---|---|---|---|---|---|---|
| 1 | W | 0.28*** | 7.02 | 13.85 | tr | tr | 0.92 | 40.41 |
|   | S | 0.82 | 10.81 | 35.60 | 0.87 | 0.92 |  | 40.41 |
| 2 | W | 0.43 | 7.15 | tr | tr | tr | Tr | 37.00 |
|   | S | 0.98 | 18.09 | 18.36 | 2.04 |  |  | 43.17 |
| 3 | W | 0.41 | Tr | 4.46 | 0.93 | 0.87 | 4.21 | 37.82 |
|   | S | 1.18 | 3.49 | 1.18 | tr | tr | tr | 57.91 |
| 4 | W | 0.56 | 0.09 | tr | tr | tr | Tr | 65.45 |
|   | S | 1.38 | 2.41 | 1.12 | tr | tr | 0.98 | 63.39 |
| 5 | W | 0.36 | 1.89 | 7.08 | tr | tr | 0.24 | 62.40 |
|   | S | 0.77 | 3.82 | 2.02 | 0.93 | tr | 2.14 | 51.21 |

*Inoculum size = 30% (15 g/50 ml medium)
**Inoculum age = 7–8 weeks after subculture of 14 month old calli
***Each value represent mean of 24 replicates pooled into 3 samples for analysis
W Wild line
S Selected line
tr Trace amounts

TABLE 4

Comparison of the efficacy of different carbohydrate energy sources (supplemented in callus maintenance medium) on biomass yield and crude ginsenoside content of wild and selected callus lines of *P. quinquefolium**

| Carbohydrate Source | Amount used | Culture age at harvest (days) | Callus line | Growth Index | Crude insenoside (% f. wt.) |
|---|---|---|---|---|---|
| Sucrose | 3% (w/v) | 20 | W | 17.82** | 0.48 |
|  |  |  | S | 36.13 | 0.59 |
|  |  | 40 | W | 40.71 | 0.31 |
|  |  |  | S | 198.23 | 0.99 |
| Market grade sugar | 3% (w/v) | 20 | W | 34.58 | 0.62 |
|  |  |  | S | 216.12 | 0.97 |
|  |  | 40 | W | 46.01 | 0.49 |
|  |  |  | S | 272.13 | 1.19 |
| Molasses after Charcoal pretreatment | 0.3% (w/v) | 20 | W | 2.16 | 0.02 |
|  |  |  | S | 8.13 | 0.13 |
|  |  | 40 | W | — | — |
|  |  |  | S | — | — |
| Molasses after EDTA Pretreatment | 0.3% (w/v) | 20 | S | — | — |
|  |  |  | W | — | — |

The main advantages of the present invention are:

1. The subject callus line in this study is capable of producing ginsenoside (within 30–50 days) in yield and quality comparable to that of 3–5 years old roots of field-grown plants.

2. It has resulted in the generation of a viable alternative source (callus line) for the commercial production of ginsenosides of *P. quinquefolium*.

3. The invention assumes significance considering the worldwide demand for *Panax saponins* and the problems associated with Panax cultivation on account of its prolonged seed dormancy and long gestation period from planting to harvest (4–7 years).

4. The cultural procedure and conditions used for this invention are fully defined and reproducible.

5. The invention provides an efficient means for ginsenoside production on large scale, irrespective of geographic locations and climatic conditions.

6. Market grade sugar can be used to replace sucrose in the medium, etc., that would contribute towards the cost reduction of the process.

What is claimed is:

1. A stable high ginsenoside-yielding callus line of *Panax quinquefolium* having:
   (a) purple pigmentation,
   (b) growth Index of 204.8 to 246.01 in about 45 days of culture,
   (c) ginsenoside yield of 0.94 to 1.33% f wt. in about 45 days of culture,
   (d) yield of Rb group of ginsenosides 49 to 55% from the crude extract in about 45 days of culture, and
   (e) yield of Rg group of ginsenoside of 35–49% from crude extact in about 45 days of culture.

2. A method for the development of a stable Panax callus line from root explants, wherein the said method comprises the steps of:

(a) establishment of the aseptic callus cultures from root explants on basal medium modified after Murashige and Skoog medium to obtain primary callus,
   (b) transferring the primary calli to growth medium for optimal growth,
   (c) multiplying and maintaining the callus for more than 2 years by regular sub-culturing in growth medium every six to seven weeks under temperature 28±2° C., 1000–2000 lux light intensity and 70 to 80% relative humidity,
   (d) obtaining the fragile and pale white calli,
   (e) isolating the high yielding purple pigmented callus occurring as spontaneous variant from $20^{th}$ sub-culture, (f) enriching the isolated purple pigmented variant through selection and cell aggregate cloning in at least seven subsequent sub-cultures, and (g) proliferating the enriched callus line by using culture medium and incubating the callus culture in continuous light of 3000–4000 lux intensity to obtain high yielding callus line.

3. A method as claimed in claim 2 wherein the root explants are obtained from at least 3 year old *Panax quinquefolium* plants.

4. A method as claimed in claim 2 wherein the roots are cut into 2–7 mm small explant pieces and are washed thoroughly in water at least 4 times to remove dirt and contaminants.

5. A method as claimed in claim 2 wherein the root explants are sterilized by treatment with centrimide for a period of about 5–10 minutes and with mercuric chloride for about 10–30 seconds.

6. A method as claimed in claim 2 wherein the basal medium in step (a) is modified Murashige and Skoog's (1962) medium supplemented with 2–4 mg/l glycine, 200 mg/l myoinositol, 10 mg/l thiamine hydrochloride, 10 mg/l pyridoxine hydrochloride and 5 mg/l nicotinic acid.

7. A method as claimed in claim 2 wherein medium II in step (b) is obtained by addition of 0.5–2.0 mg/l 2,4-dichlorophenoxyacetic acid, and 0.25–0.50 mg/l kinetin to the basal medium for optimal callus induction.

8. A method as claimed in claim 2 wherein culture medium comprises nutrient salts of basal medium, 200 mg/l myoinositol, 2.0–4.0 mg/l glycine, 0.5–1.0 mg/l nicotinic acid, 0.5–2.0 mg/l pyridoxine HCl and 0.2–0.4 mg/l thiamine HCl, 0.1–0.5 mg/l, 2,4-D, and 0.25–0.50 mg/l Kinetin for optimal growth of the selected line.

9. A method as claimed in claim 2 wherein the carbohydrate sources are selected from sucrose, molasses treated with EDTA and charcoal and, market grade sugar.

10. A method for the extraction of crude ginsenoside from high yielding Panax callus lines as claimed in claim 2 by known methods.

11. A stable Panax callus line made according to the method of claim 2.

12. A stable Panax callus line made according to the method of claim 3.

13. A stable Panax callus line made according to the method of claim 4.

14. A stable Panax callus line made according to the method of claim 5.

15. A stable Panax callus line made according to the method of claim 6.

16. A stable Panax callus line made according to the method of claim 7.

17. A stable Panax callus line made according to the method of claim 8.

18. A stable Panax callus line made according to the method of claim 9.

* * * * *